US006057767A

United States Patent [19]

Barnoach

[11] Patent Number: 6,057,767

[45] Date of Patent: May 2, 2000

[54] SNORING PREVENTION AND SLEEP POSTURE ALERT APPARATUS

[76] Inventor: Izhak Barnoach, Ahi Dakar 4, Uerzliya 46702, Israel

[21] Appl. No.: 09/126,082

[22] Filed: Jul. 30, 1998

[51] Int. Cl.[7] .......... G08B 23/00

[52] U.S. Cl. .......... 340/575; 340/573.1; 340/573.7

[58] Field of Search .......... 340/573.1, 573.5, 340/573.7, 575, 686.1, 689, 527, 529; 128/846, 848; 600/529, 534, 587, 595

[56] References Cited

U.S. PATENT DOCUMENTS

| | | | |
|---|---|---|---|
| 4,617,525 | 10/1986 | Lloyd | 340/573.1 |
| 4,713,890 | 12/1987 | Wells et al. | 33/366.25 |
| 4,938,476 | 7/1990 | Brunelle et al. | 482/148 |
| 4,941,478 | 7/1990 | Takeuchi et al. | 128/848 |
| 5,081,447 | 1/1992 | Echols | 340/573.7 |
| 5,373,859 | 12/1994 | Forney | 128/846 |
| 5,381,801 | 1/1995 | McShane et al. | 128/848 |
| 5,684,460 | 11/1997 | Scanlon | 340/573.1 |
| 5,684,461 | 11/1997 | Jones | 340/575 |
| 5,914,660 | 6/1999 | Mesibov et al. | 340/573.1 |

*Primary Examiner*—Daniel J. Wu
*Assistant Examiner*—Van T. Tried
*Attorney, Agent, or Firm*—Foley & Lardner

[57] ABSTRACT

This invention relates to an apparatus for preventing snoring and for alerting when an infant sleeps on his back. The apparatus for preventing snoring is comprised of a gravity actuated sensor, a delay time circuit and a vibrator, which are placed within a housing. The apparatus is worn by its user, and the gravity activated sensor senses when it is in a predetermined range of deviation from the horizontal, and sends a detect signal to the time delay circuit. If the detect circuit lasts for a longer period than a predetermined interval, the delay time circuit activates a vibrator which irritates the apparatus user, causes him to change his sleep posture, without waking him. The apparatus for alerting when an infant sleeps on his back is comprised of two parts. The first part is comprised of a gravity actuated sensor, a delay time circuit and a transmitter, which are placed within a housing. The first part is analogous to apparatus for preventing snoring but has a transmitter instead of vibrator. The transmitter sends a signal to the second part of the apparatus, which is worn by another person. The receiver activates a vibrator which awakens the other person.

10 Claims, 8 Drawing Sheets

20

SNORING PREVENTION AND SLEEP POSTURE ALERT APPARATUS

THE FIELD OF THE INVENTION

The invention relates to an apparatus for preventing snoring and for alerting when an infant sleeps on his back.

BACKGROUND OF THE INVENTION

It is well known that snoring is often worse and is often triggered when a person sleeps on his back. Some of the devices for preventing snoring are based on that fact. For example, U.S. Pat. No. 5,381,801 of McShane et al. describes an electromagnetic tactile stimulation device worn on a belt for the prevention of snoring. The device is relatively complicated, is uncomfortable and awkward. The device is based on a pressure sensor. One of the disadvantages of pressure sensors is the need of more than one sensor for sensing, in an efficient manner, when the user of the device sleeps on his back.

U.S. Pat. No. 4,938,476 of Brunell et al. describes a body position attitude indicator which activates a buzzer to alert the user when he deviates a set angular amount from a vertical position. The main disadvantage of that device is the usage of a buzzer. If a person is a sound sleeper or hard of hearing, a buzzer is not very effective. A buzzer can also disturb a person sleeping near the user of the device. Another disadvantage of the device is its awkward shape, making it unpleasant to wear.

U.S. Pat. No. 4,617,525 of Lloyd describes a sleep posture monitor and alarm system which awakes its user when he attempts to sleep in a particular sleep posture. The main disadvantage of this system is that it awakes the sleeper. The sleeper is awakened in order to train him not to sleep on a particular sleep posture.

It is well known that infants can die during sleeping. This phenomena is known as cradle death. Sleeping on the back increases the chance of cradle death. There is a need to awake another person, such as the infant's mother, when an infant sleeps on his back, so that the other person can check the infant and may alter the infants position.

There is a need of an improved apparatus for preventing snoring, of compact size. There is a need of an improved apparatus for preventing snoring, which does not awaken its user or a person sleeping in the user proximity. There is a need of an improved apparatus which wakens a person when an infant sleeps on its back.

SUMMARY OF THE INVENTION

The invention solves the problems mentioned above by applying the features laid down in the independent claims. Preferred embodiments are given in the dependent claims.

An advantage of the invention is that it provides a compact apparatus for preventing snoring. Yet another advantage of the invention is that it provides an apparatus which does not awake its user or a person sleeping in the user proximity. Yet a further advantage of the invention is that it provides an apparatus which wakens a person when an infant sleeps on its back.

DETAILED DESCRIPTION OF THE DRAWINGS

Figure 1:
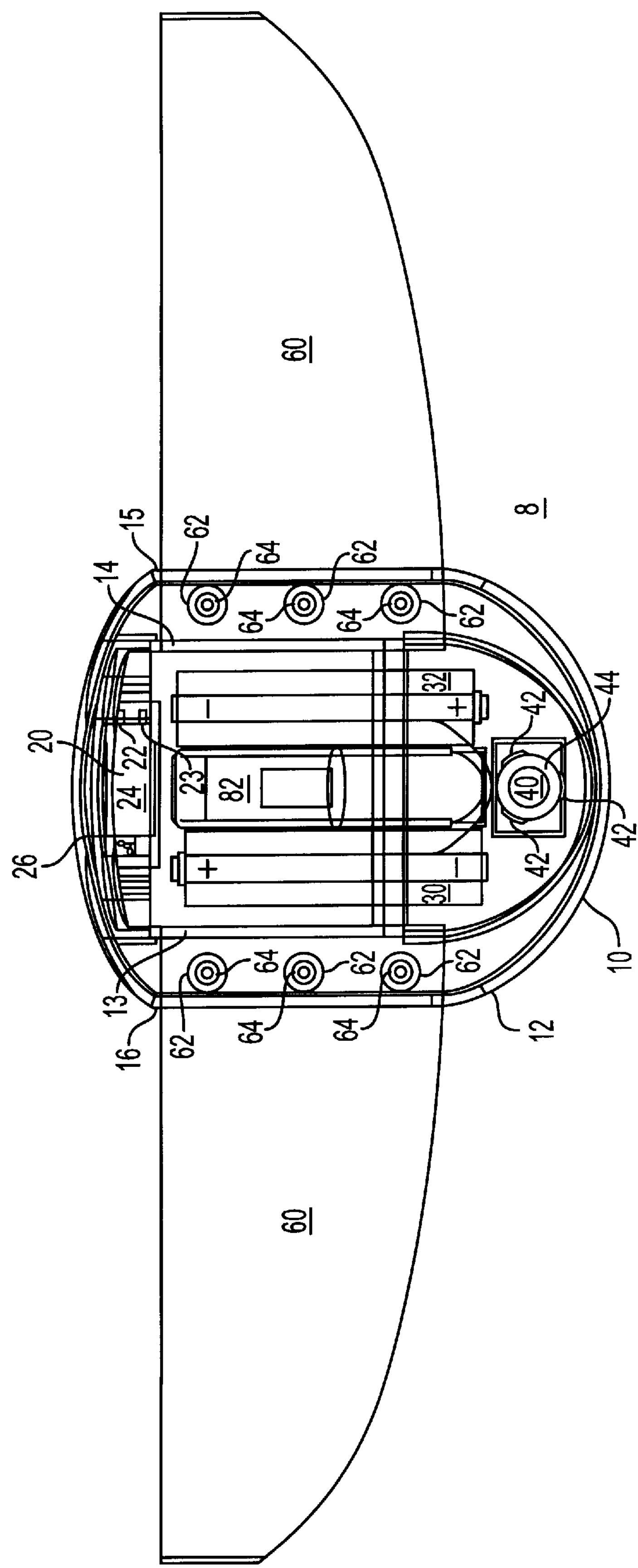
FIG. 1 is a top sectional view of an apparatus for preventing snoring, according to a preferred embodiment of the invention.
Figure 2:
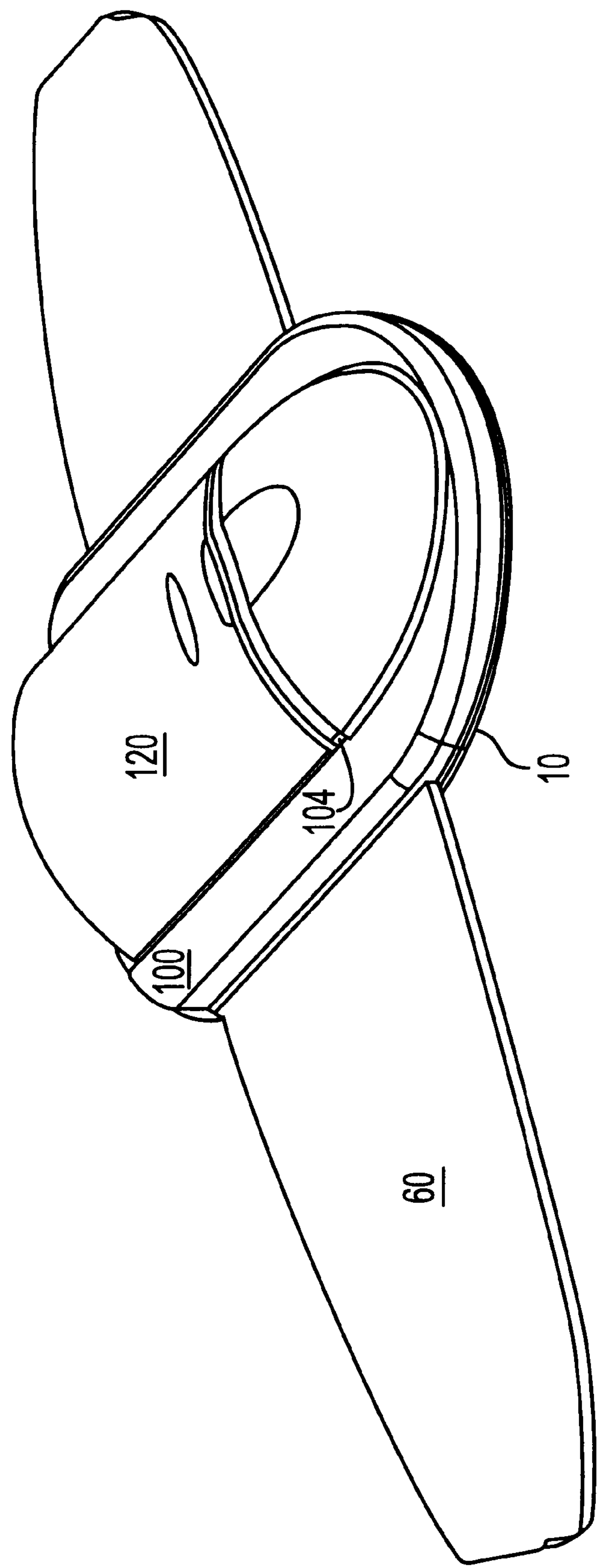
FIG. 2 is a perspective view of the housing of the apparatus for preventing snoring, according to a preferred embodiment of the invention.
Figure 3:
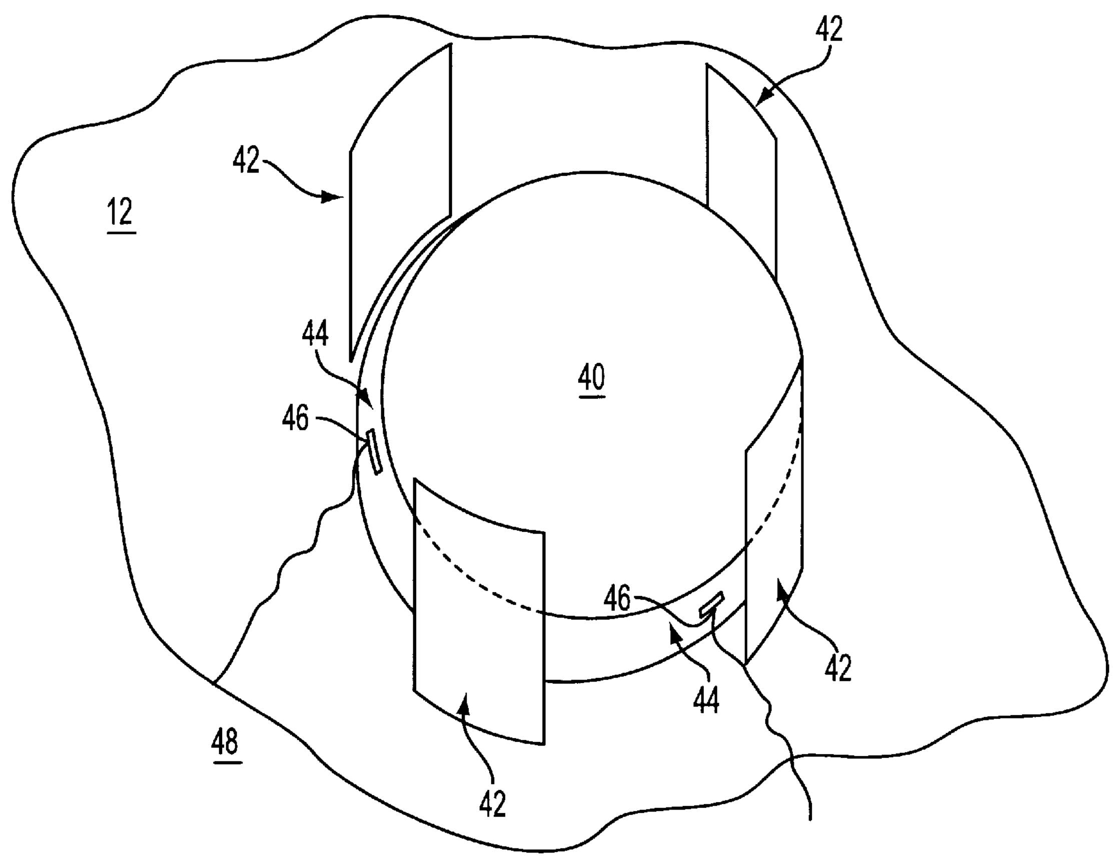
FIG. 3 is a perspective view of the gravity actuated sensor of the apparatus for preventing snoring, according to a preferred embodiment of the invention.

Referring to FIGS. 1 and 2, a preferred embodiment of the invention comprises a housing 10, having a lower part 12 and an upper part 100 (shown in FIGS. 2, 3). Lower part 12 has two vertical limiters 13 and 14, two slots 15 and 16, for receiving a belt 60, a recess 44 (not shown in FIG. 1) and a plurality of vertical pins 64. Vibrator 20, has inputs 22 and 23, a motor 24 having shaft 26 (shown in FIG. 5) connected to asymmetrical load 28. Batteries are labeled 30 and 32. A conductive object, preferably shaped as a ball (i.e.- conductive ball) 40 is retained by a plurality of limiters 42. Belt 60 has a plurality of holes 62 for attaching the belt ends to the housing. An electrical circuit 82 comprises a detect signal driver 131, a time delay circuit 161 and a vibrator driver (all shown in FIG. 4 or FIG. 5).

Belt 60 is used to attach the apparatus 8 to the apparatus user. Belt 60 is preferably made of a flexible material. Belt 60 is described only for convenience of explanation and there can be a variety of attachment means for attaching the apparatus 8 to its user. For example, apparatus 8 can be placed in a pocket on the front side of its user's shirt. Belt 60 has a plurality of holes 62, which fit the pins 64 of the lower part of the housing 12.

The vertical limiters 13 and 14 of lower part 12 of housing 10 are used to support the power supply means, preferably batteries 30 and 32.

Batteries 30 and 32 are coupled to electrical circuit 82, for energizing electrical circuit 82 and vibrator 20.

Vibrator 20 has inputs 22 and 23, coupled to vibrator driver 181, for receiving D.C. voltage. When there is sufficient voltage differential between inputs 22 and 23, motor 24 is activated. Motor 24 drives an asymmetrical load 28, and produces vibrations. Load 28 can also be made of an eccentrically balanced wheel. Conveniently, motor 24 is relatively small and revolves in a high frequency, so that the vibrations irritate the user of apparatus 8, cause him to change his position, but do not awake him. A series of vibrations can train the user not to sleep on his back.

Conductive ball 40, limiters 42 and recess 44 form a gravity actuated sensor 48 (shown in FIG. 4) for sensing when apparatus 8 is in a predetermined range of deviation from the horizontal. Apparatus 8 is attached to its user so that this deviation occurs when its user sleeps in a predetermined posture, preferably on his back. Conductive ball 40 can freely move in a space defined by recess 44, limiters 42 and upper part 100 of housing 10. Recess 44 is formed in lower part 12 of housing 10. Limiters 42 surround recess 44, and preferably are perpendicular to lower part 12 of housing 10. The distance between two consecutive limiters is smaller than the diameter of conductive ball 40, and is preferably less than the radius of conductive ball 40. Limiters 42 are made of non conductive material. Conveniently, recess 44 is shaped according to the shape of conductive ball 40, so that conductive ball 40 will remain in recess 44 as long as the user of apparatus 8 is in a predetermined range of deviation from the horizontal. When the user is outside of that range, conductive ball 40 exits recess 44. Preferably, the recess 44 is of circular shape and is slightly bigger than the conductive ball 40. Preferably, the depth of recess 44 equals one half of the radius of the conductive ball 40. The predetermined range of deviation mentioned above can be changed by changing the shape of recess 44, and/or conductive ball 40, or by changing the position of apparatus 8 in relation to its user. Those who are skilled in the art will appreciate that conductive ball 40, and accordingly recess 44, can have different shapes. Those who are skilled the art will appreciate that if the space defined by recess 44, limiters 42 and upper part 100 of housing 10, is sealed, conductive ball 40 can be replaced by a conductive fluid.

At least two electrodes 46 are placed within recess 44, wherein as long as conductive ball 40 is in the recess, it closes an electrical circuit across electrodes 46. As explained in further detail in FIG. 4, the closing of an electrical circuit generates a detect signal.

Those who are skilled in the art will appreciate that gravity actuated sensor 48 can be implemented in various ways. For example, and without limiting the scope of the invention, gravity actuated sensor 48 can be implemented by a mercury switch. The mercury switch has a sealed and non conductive housing. In one end of the housing there are two electrodes. The first electrode is placed at a short distance from the second electrode. Within the housing there is a small amount of mercury. When the user of apparatus 8 is in a predetermined range of deviation from the horizontal, the mercury moves into contact with the two electrodes and closes an electrical circuit across the electrodes.

As a further example, and without limiting the scope of the invention, gravity actuated sensor 48 can be implemented by two conductive parts. The first part is a free swinging pendulum. The second part is a conductive plate or ring which is placed near the free swinging pendulum, in a manner that it will make contact with the free swinging pendulum, when the pendulum swings out of a predetermined vertical amount. This predetermined vertical amount reflects the predetermined range of deviation from the horizontal of the apparatus user.

It is desired to reject short detect signals, which can result from momentary sleep postures, and activate the vibrator just when long detect signals appear. For example, if the user of apparatus 8 lies on his back for a short period while rolling from a sleep posture on one of his side to the other. As explained in further detail in regard to FIG. 4, the detect signal is sent from gravity actuated sensor 48 to a time-delay circuit 161. The detect signal can be sent from the gravity actuated sensor 48, through a detect signal driver 131 and to the time delay circuit 161. The time delay circuit rejects short detect signals and sends an enable signal to vibrator driver 181 only if the detect signal appears only for a longer time period than a predetermined period (i.e.- a long detect signal). The time delay circuit can be implemented by a variety of low frequency pass filters.

FIG. 2 is a perspective view of housing 10 of apparatus 8 for preventing snoring, according to a preferred embodiment of the invention. Housing 10 has an upper part 100, a lower part 12 and a battery cover 120. Battery cover 120 is connected to a conductive plate 127 (not shown in FIG. 2). Two rails 104 are connected to upper part 100. Rails 104 are parallel to each other and perpendicular to upper part 102 of the housing 10. Battery cover 120 can move along rails 104. Preferably, battery cover 120 has three positions: "ON" in which the conductive plate 127 connects batteries 30 and 32 to electrical circuitry 82, "OFF", in which conductive plate 127 disconnects batteries 30 and 32 from electrical circuitry 82, and a third position in which battery cover 120 is removed from housing 10, allowing the replacement of batteries 30 and 32.

Housing 10 is relatively slim, compact and it is convenient to wear.

Housing 10 is described for convenience of explanation only and any housing, having an ON/OFF switch and a hatch for replacing batteries 30 and 32 can be implemented.

FIG. 3 is a perspective view of gravity actuated sensor 48 of apparatus 8, according to a preferred embodiment of the invention. Gravity actuated sensor 48 comprises conductive ball 40, limiters 42, recess 44 and electrodes 46.

Figure 4:
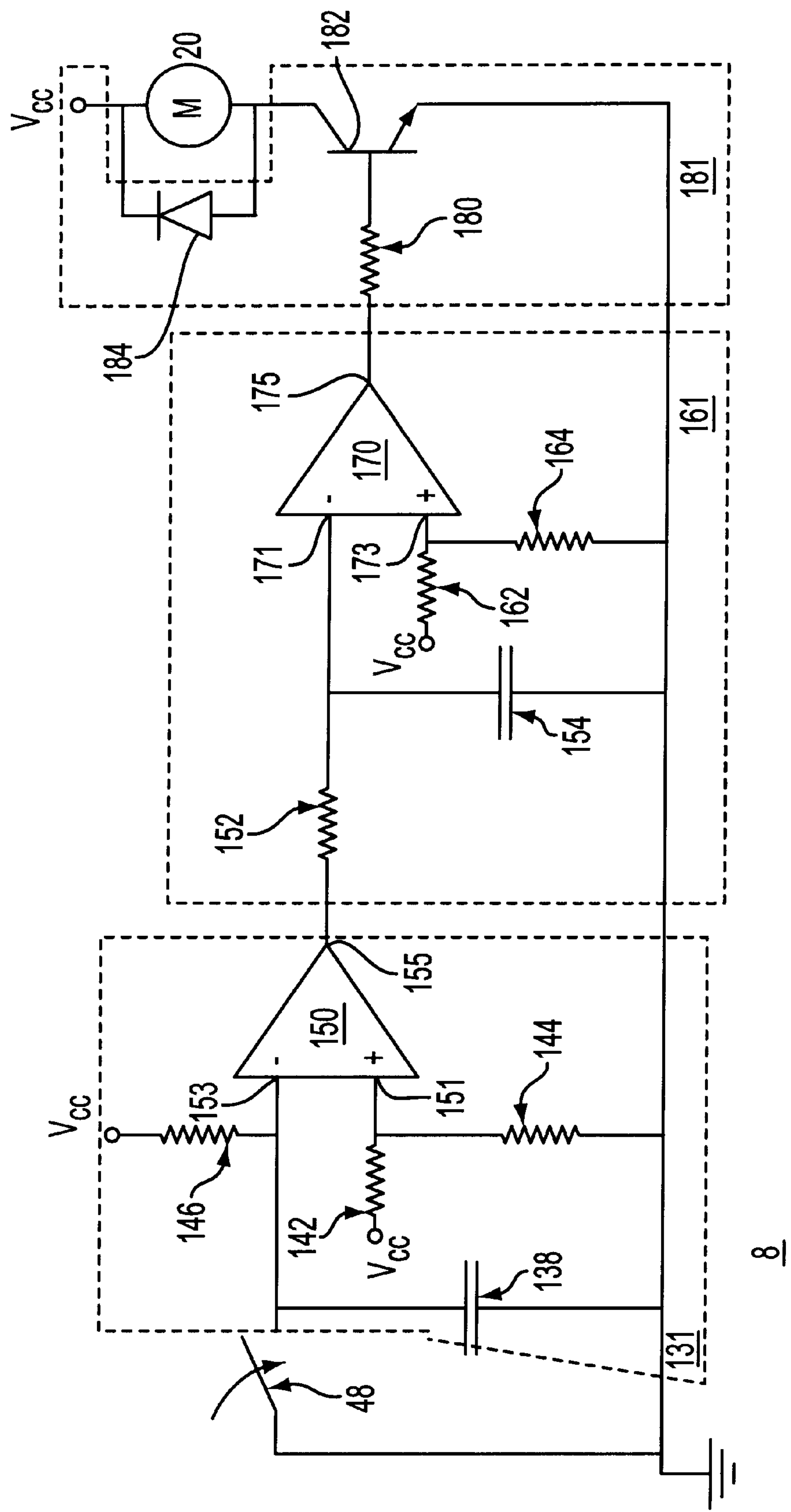
FIG. 4 is an electrical schematic description of the apparatus for preventing snoring, according to a preferred embodiment of the invention.

FIG. 4 is a schematic description of apparatus 8, according to a preferred embodiment of the invention, comprising gravity actuated sensor 48, detect signal driver 131, time delay circuit 161 and vibrator driver 181. Each of these parts can be implemented by various ways, and just for convenience of explanation one embodiment is described in further detail. Detect signal driver 131 is not essential, and gravity actuated sensor 48 can be coupled directly to time delay circuit 161.

Gravity actuated sensor 48 is comprises recess 44, limiters 42 and upper side 100 of housing 10 (not shown in FIG. 4), a conductive ball 40 and at least first and second electrodes 46' and 46".

Detect signal driver 131, for smoothing the detect signal, comprises first capacitor 138, first resistor 142 and a second resistor forming a first resistive voltage divider 140, a pull-up resistor 146 and a first comparator 150, having positive input 151, a negative input 153 and output 155.

Time delay circuit 161 comprises charging resistor 152, second capacitor 154, third resistor 162 and fourth resistor 164 forming a second resistive voltage divider 160, and second comparator 170, having positive input 171, a negative input 173 and output 175.

Vibrator driver 181 comprises bias resistor 180, transistor 182, diode 184 and inputs 22 and 23 of vibrator 20.

The voltage supply described in FIG. 4 is batteries 30 and 32 (not shown in FIG. 4), which are connected or disconnected to electrical circuit 82 by conductive plate 127 (not shown in FIG. 4) which is coupled to battery cover 120 (not shown in FIG. 4). Batteries 30 and 32 can be coupled to a voltage measurement means (shown in FIG. 5), for measuring the voltage level supplied by batteries 30 and 32, and sending an alert signal when batteries 30 and 32 are going to expire. For example, and without limiting the scope of the invention, the voltage measurement means can be coupled to a plurality of light emitting diodes (i.e.- LED's) which can indicate the voltage level.

First electrode 46' is coupled to the ground and the second electrode is coupled to negative input 153 of first comparator 150, and to one end of pull-up resistor 146. The other end of pull-up resistor 146 is coupled to the voltage supply 30 and 32. One end of first resistor 142 of first resistive voltage divider 140 is coupled to power supply 30 and 32 and the other end is coupled to positive input 151 of first comparator 150. One end of second resistor 142 of first resistive voltage divider 140 is coupled to the ground and the other end is coupled to positive input 151 of first comparator 150. Output 152 of first comparator 150 is coupled to one end of charging resistor 152. One end of capacitor 154 is coupled to the ground and the other is coupled to the second end of charging resistor 152 and to positive input 171 of second comparator 170. One end of first resistor 162 of second resistive voltage divider 160 is coupled to power supply 30 and 32, and the other end is coupled to negative input 173 of second comparator 170. One end of second resistor 162 of second resistive voltage divider 160 is coupled to the ground and the other end is coupled to negative input 173 of second comparator 170. Output 175 of second comparator 170 is coupled to one end of bias resistor 180. The other end of bias transistor 180 is coupled to the base of transistor 182. The collector of transistor 182 is coupled to first input 22 of vibrator 20. Power supply 30 and 32 is coupled to second input 23 of vibrator 20. The cathode of diode 184 is coupled to power supply and the anode of diode 184 is coupled to the collector of transistor 182.

When conductive ball 40 does not close an electrical circuit between electrodes 46' and 46, pull up resistor 146 charges first capacitor 138 until the voltage level arriving to negative input 153 of first comparator 150 equals the power supply voltage. First resistive voltage divider 140 divides the power supply voltage and inputs a reference voltage, which is lower than the power supply voltage, to positive input 151 of first comparator 150. Because the voltage level input to positive input 151 of first comparator 150 is lower than the voltage level input to negative input 153 of first comparator 150, the output level of first comparator 150 is low. The low level of the output of first comparator 150 holds second capacitor 154 discharged, and holds the output of second comparator 170 low. This low output causes transistor 182 to be in a cut off state. When transistor 182 is cut-off there is almost no voltage differential between inputs 23 and 22 of vibrator 20, so that the vibrator is not activated.

When conductive ball 40 closes the electrical circuit between electrodes 46' and 46", it generates a detect signal by pulling negative input 153 of first comparator 150 to ground and drives output 155 of first comparator 150 to be high. This high output charges second capacitor 154, through charging resistor 152. When the voltage of second capacitor 154 is higher than the reference voltage created by second resistive voltage divider, the time delay is completed and the output signal of second comparator 170 turns to high. This high signal forces transistor 182 to saturate, creates a voltage differential between two inputs 22 and 23 of vibrator 20, and activates vibrator 20.

Figure 5:
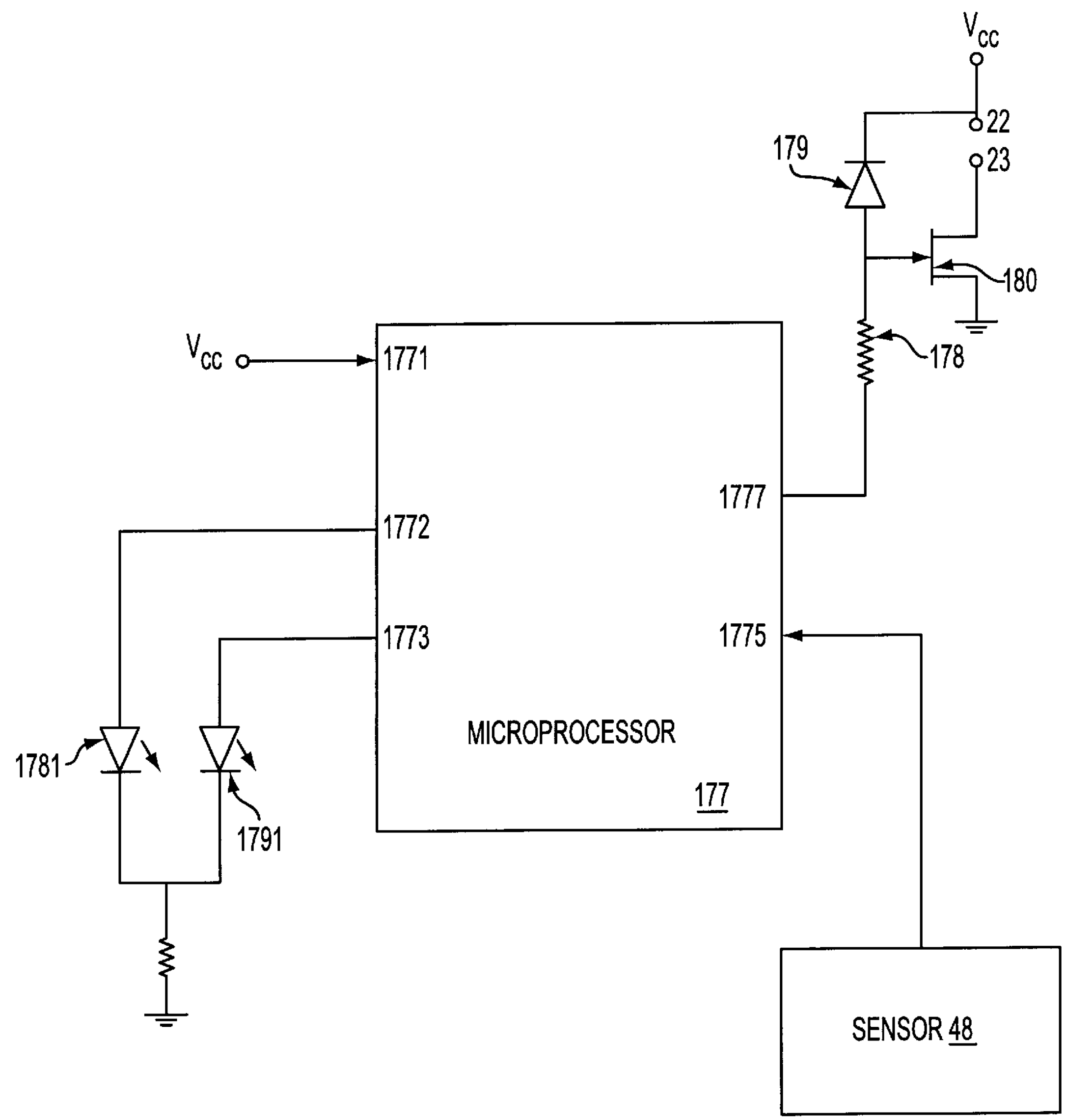
FIG. 5 is an electrical schematic description of the apparatus for preventing snoring, according to another preferred embodiment of the invention.

FIG. 5 is an electrical schematic description of the apparatus for preventing snoring, according to another preferred embodiment of the invention. Microprocessor 177, has vcc input 1771, for receiving supply voltage; vibrator output 1777 and sensor input 1775 for receiving detect signals from sensor 48. Microprocessor 177 can also have a plurality of LED outputs 1772 and 1773, for driving a plurality of LEDs 1781 and 1791. LEDs 1781 and 1791 are used to indicate the level of voltage supplied by batteries 30 and 32. Microprocessor 177 can perform the functions of detect signal driver 131 and time delay circuit 161, shown in FIG. 4. Microprocessor 177 can have an internal memory for storing a series of instructions which operate microprocessor 177.

Figure 6:
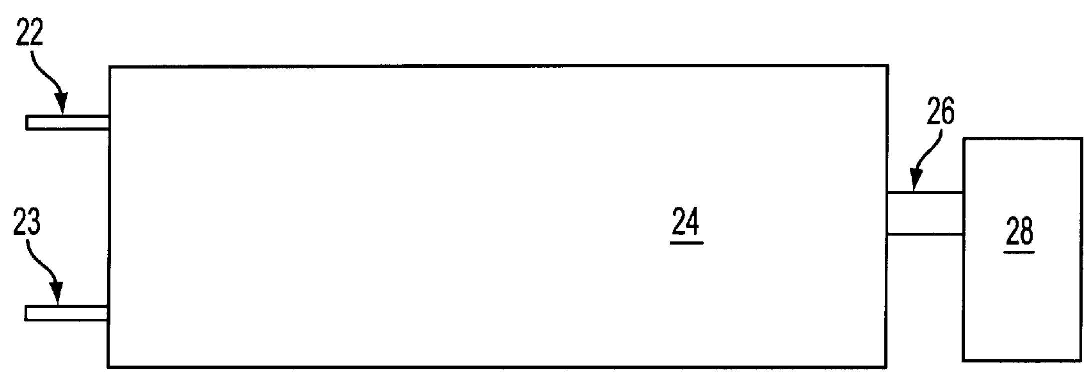
FIG. 6 is a top plan view of the vibrator of the apparatus for preventing snoring, according to a preferred embodiment of the invention.

Vibrator output 1777 is coupled to resistor 178, diode 179 and power-transistor 180 for driving vibrator 20 (Shown in FIG. 6).

FIG. 6 is a top plan view of vibrator 20, according to a preferred embodiment of the invention. Vibrator 20 has inputs 22 and 23, a motor 24 having shaft 26 and an asymmetrical load 28 on shaft 26.

Figure 7:
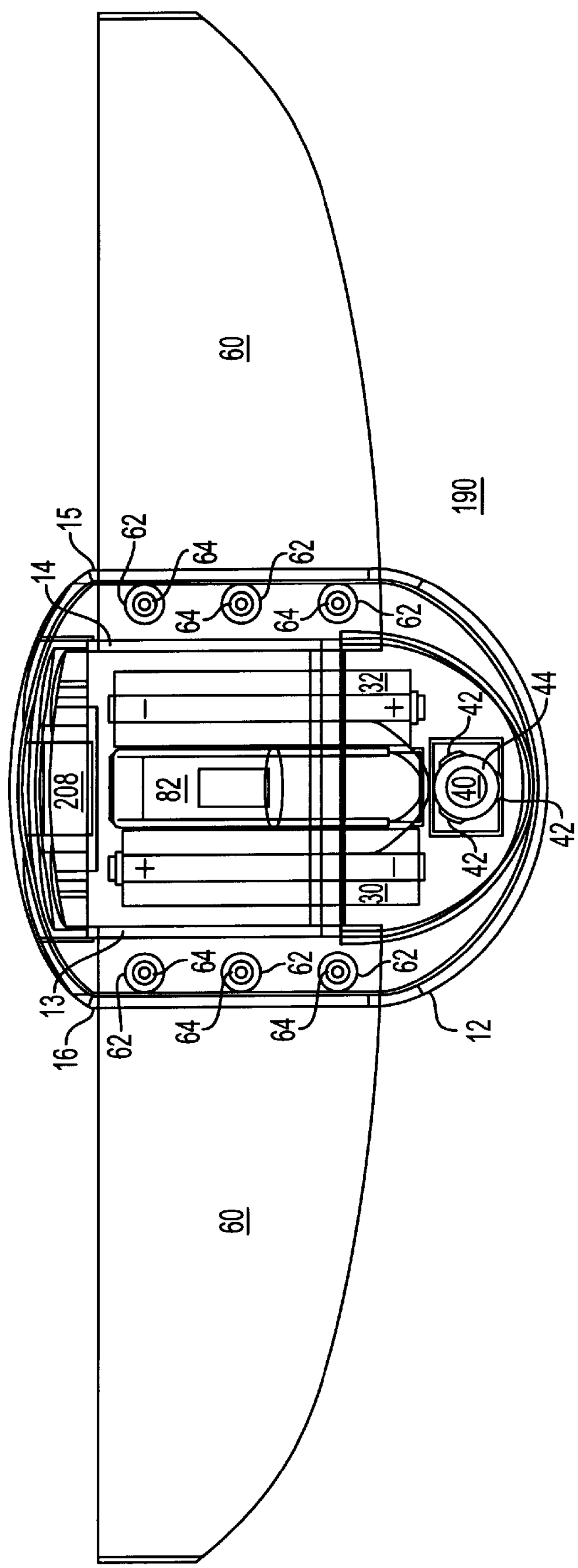
FIG. 7 is a top sectional view of an a first section of a apparatus for alerting when an infant sleeps on his back, according to a preferred embodiment of the invention.
Figure 8:
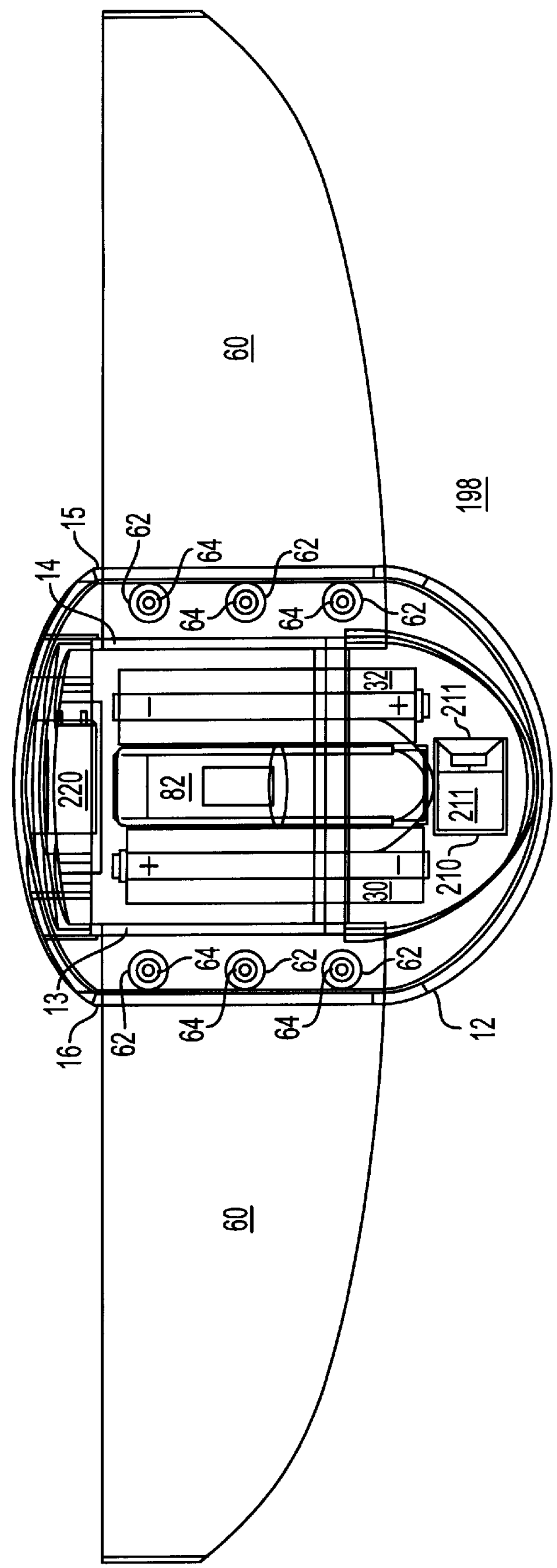
FIG. 8 is a top sectional view of a second section of a apparatus for alerting when an infant sleeps on his back, according to a preferred embodiment of the invention.

FIG. 7 is a top sectional view of a first part 190 of device 200 for alerting when an infant sleeps on his back, according to a preferred embodiment of the invention. Second part 198 of device 200 is shown in FIG. 8. First part 190 is analogous to apparatus 8, but has a transmitter 208 instead of vibrator 20. First part 190 is worn by the infant. When the infant sleeps on his back, transmitter 208 sends a signal to the second part 198. The same reference numbers are used to identify like elements in the drawings.

The housing of first part 190 is analogous to housing 100 of apparatus 8 (shown in FIG. 2). The sensor of first part 190 of device 200 is analogous to sensor 48 of apparatus 8 (shown in FIG. 3). The electrical circuitry of first part 190 is analogous to electrical circuit 82 of apparatus 8 (shown in FIG. 4), but the transistor is coupled to transmitter 208 instead of vibrator 20.

FIG. 8 is a top sectional view of an a second part 198 of device 200 for alerting when an infant sleeps on his back, according to a preferred embodiment of the invention. Second part 198 comprises a receiver 210 and an awake vibrator 220. Awake vibrator 220 is analogous to vibrator 20 of apparatus 8, but it awakens its user. Awake vibrator 220 has more torque than vibrator 8, and it revolves at lower frequencies.

Those who are skilled in the art will appreciate that various changes in form and detail can be made without departing from the spirit and scope of the invention which is determined in the claims that follow.

What is claimed is:

1. An apparatus for preventing snoring, when the apparatus is attached to a user, the apparatus comprising:

a housing;

a gravity actuated sensor, placed within the housing, for sensing when the user sleeps on his back, and sending a detect signal;

a time delay circuit, placed within the housing and coupled to the gravity actuated sensor, for rejecting short detect signals;

a vibrator, for producing high frequency vibrations which irritate the user of the apparatus and cause him to change his sleep posture without awakening him;

a vibrator driver, placed within the housing and coupled to the time delay circuit and to the vibrator, for activating the vibrator as a result of long detect signals; and a power supply means, placed within the housing, and coupled to the gravity actuated sensor, to the time delay circuit and to the vibrator driver.

2. The apparatus of claim 1 wherein the gravity actuated sensor comprises:

a conductive object;

a recess, made of non conductive material;

at least two electrodes, placed within the recess;

a plurality of limiters, which surround the recess;

wherein the recess, the limiters and a part of the housing form a space in which the conductive object can freely move;

wherein when the apparatus is in a predetermined range of deviation from the horizontal, the conductive object is forced by gravity to be in the recess; and wherein when the conductive object is in the recess it closes a electrical circuit across the electrodes.

3. The apparatus of claim 2 wherein the conductive object is a conductive ball.

4. The apparatus of claim 1 wherein the gravity actuated sensor is a mercury switch comprising:

a small amount of mercury;

a sealed and non conductive housing, having more than one end;

two electrodes which are placed in one end of the housing; wherein the first electrode is placed at a short distance from the second electrode;

wherein the mercury is within the housing; and wherein when the apparatus is in a predetermined range of deviation from the horizontal, the mercury moves into contact with the two electrodes and closes an electrical circuit across the electrodes.

5. The apparatus of claim 1 wherein the gravity actuated sensor comprises two conductive parts;

wherein one of said conducting parts is a free swinging pendulum;

wherein another of said conductive parts is a conductive plate;

wherein the conductive plate is placed near the free swinging pendulum, in a manner such that it will make contact with the free swinging pendulum, when the free swinging pendulum swings beyond a predetermined range; and wherein movement of said pendulum beyond said predetermined range corresponds to a position of the user on his back.

6. The apparatus of claim 1 wherein a detect signal driver is connected between the gravity actuated sensor and the time delay circuit, for smoothing the detect signal.

7. The apparatus of claim 6 wherein the apparatus has at least two electrodes, wherein the gravity actuated sensor closes an electrical circuit across the electrodes when it senses that the apparatus is in a predetermined range of deviation from the horizontal;

wherein the detect signal driver comprises: a first capacitor, a first resistor , a second resistor, a pull-up resistor and a first comparator , having positive input, a negative input and output; wherein the first and second resistor form a first resistive voltage divider;

wherein the time delay circuit comprises: a charging resistor, a second capacitor, a third resistor, a fourth resistor, and a second comparator , having positive input, negative input and output; wherein the third and fourth resistor form a second resistive voltage divider;

wherein the vibrator driver comprises: a bias resistor, a transistor, a diode and a plurality of outputs coupled to the vibrator inputs;

wherein a first electrode is coupled to the ground and a second electrode is coupled to the negative input of the first comparator, and to one end of the pull-up resistor; wherein the other end of the pull-up resistor is coupled to the power supply;

wherein one end of the first resistor is coupled to the power supply and the other end is coupled to the positive input of the first comparator; wherein one end of the second resistor is coupled to the ground and the other end is coupled to the positive input of the first comparator;

wherein the output of the first comparator is coupled to one end of the charging resistor; wherein one end of the capacitor is coupled to the ground and the other is coupled to second end of the charging resistor and to the positive input of the second comparator; wherein one end of the third resistor is coupled to the power supply and the other end is coupled to the negative input of the second comparator; wherein one end of the fourth resistor is coupled to the ground and the other end is coupled to the negative input of the second comparator;

wherein the output of the second comparator is coupled to one end of the bias resistor and the other end of the bias transistor is coupled to the base of the transistor; wherein the collector of the transistor is coupled to the first input of the vibrator; and wherein the power supply is coupled to the second input of the vibrator; wherein the cathode of diode is coupled to the power supply and the anode of the diode is coupled to the collector of transistor.

8. The apparatus of claim 1 further comprising a voltage measurement means and an indicator;

wherein the power supply means is coupled to the voltage measurement means for measuring the voltage supply level; and wherein the indicator is coupled to the voltage measurement means for indicating what is the voltage supply level.

9. The apparatus of claim 1 wherein the housing has an upper part, a lower part, two rails, a conductive plate and a battery cover;

wherein the battery cover is connected to the conductive plate;

wherein the two rails are connected to the upper part;

wherein the two rails are parallel to each other and perpendicular to the upper part of the housing; and wherein the battery cover can move along the two rails.

10. The apparatus of claim 9 wherein the battery cover has three possible positions:

an 'ON' position in which the conductive plate connects the power supply to the electrical circuitry;

an 'OFF' position in which the conductive plate disconnects the power supply from the electrical circuitry; and a third position in which the battery cover is removed from housing, allowing the replacement of the power supply.

* * * * *